(12) United States Patent
Andersen (10) Patent No.: US 8,529,875 B2
(45) Date of Patent: Sep. 10, 2013

(54) TOBACCO ALKALOID RELEASING CHEWING GUM

(75) Inventor: Carsten Andersen, Vejle (DK)

(73) Assignee: Fertin Pharma A/S (DK)

( * ) Notice: Subject to any disclaimer, the term of this patent is extended or adjusted under 35 U.S.C. 154(b) by 1295 days.

(21) Appl. No.: 11/631,056

(22) PCT Filed: Jun. 29, 2005

(86) PCT No.: PCT/DK2005/000442
§ 371 (c)(1),
(2), (4) Date: Dec. 27, 2006

(87) PCT Pub. No.: WO2006/000232
PCT Pub. Date: Jan. 5, 2006

(65) Prior Publication Data
US 2009/0196834 A1    Aug. 6, 2009

(30) Foreign Application Priority Data
Jun. 29, 2004 (DK) ................................ 2004 01022

(51) Int. Cl.
*A61K 9/58* (2006.01)
(52) U.S. Cl.
USPC ............................ 424/48; 424/78.15; 514/243
(58) Field of Classification Search
USPC .............................................................. 426/5
See application file for complete search history.

(56) References Cited

U.S. PATENT DOCUMENTS

| 3,845,217 | A | 10/1974 | Ferno et al. | |
| 3,877,468 | A | 4/1975 | Lichtneckert et al. | |
| 3,901,248 | A | 8/1975 | Lichtneckert et al. | |
| 4,971,806 | A | 11/1990 | Cherukuri et al. | |
| 5,487,902 | A * | 1/1996 | Andersen et al. | 426/3 |
| 5,488,962 | A | 2/1996 | Perfetti | |
| 6,344,222 | B1 | 2/2002 | Cherukuri et al. | |
| 6,627,234 | B1 * | 9/2003 | Johnson et al. | 426/5 |
| 6,986,907 | B2 | 1/2006 | Phillips et al. | |
| 7,056,542 | B1 | 6/2006 | Bridger et al. | |
| 2002/0098264 | A1 * | 7/2002 | Cherukuri et al. | 426/3 |
| 2004/0115305 | A1 | 6/2004 | Andersen et al. | |
| 2004/0194793 | A1 * | 10/2004 | Lindell et al. | 131/270 |
| 2005/0220934 | A1 * | 10/2005 | Leadbeater et al. | 426/3 |

FOREIGN PATENT DOCUMENTS

| WO | 9317571 A1 | 9/1993 |
| WO | WO 00/25598 | 5/2000 |
| WO | 0057842 A2 | 10/2000 |
| WO | WO 02/076229 | 10/2002 |
| WO | WO 02/102357 | 12/2002 |

(Continued)

OTHER PUBLICATIONS

Fiedler, H.P., Lexikon der Hilfsstoffe für Pharmacie, Kosmetik und Angrenzende Gebiete (1981) pp. 63-64.

(Continued)

*Primary Examiner* — Frederick Krass
*Assistant Examiner* — Michael P Cohen
(74) *Attorney, Agent, or Firm* — St. Onge Steward Johnston & Reens LLC (57) ABSTRACT

The invention relates to a tobacco alkaloid releasing chewing gum comprising tobacco alkaloid, gum base, and chewing gum ingredients, said gum base comprising elastomer and resin-compounds constituting an amount in the range of about 2 to 20% by weight of said chewing gum.

64 Claims, 1 Drawing Sheet

(56) References Cited

FOREIGN PATENT DOCUMENTS

| WO | WO02/102357 | * | 12/2002 |
|---|---|---|---|
| WO | 2004004480 A1 | | 1/2004 |
| WO | WO 2004/056363 | | 7/2004 |
| WO | WO 2006/058536 | | 6/2006 |

OTHER PUBLICATIONS

Food and Drug Administration, CFR Title 21, Sec. 172.615 (Apr. 1, 2007) pp. 66-68.
Office Communication, Application Serial No. 05 753 675.7 dated Dec. 19, 2007.
Preliminary Report dated Jun. 27, 2007 for Application No. PCT/DK2005/000442.
Written Opinion dated Oct. 17, 2005 for Application No. PCT/DK2005/000442.
Notification dated Jul. 27, 2005 for Application No. PCT/DK2005/000442.
Martindale, The Extra Pharmacopoeia, 28th edition, 1982, pp. 547-548.
Manly et al., "Substances Capable of Decreasing the Acid Solubility of Tooth Enamel", J. Dent. Res., vol. 28, No. 2, Apr. 1949, pp. 160-171.
Hunter et al., "Calcium Channel Blockers 1: A Review of Their Mechanisms of Action", Pharmacy International, Nov. 1985, pp. 267-271.
US Federal Regulations, Title 21, Section 182.8013-182.8997, printed Oct. 26, 2005, (3 pages).
International Search Report; International Application No. PCT/DK2005/000442; Date of Completion of Search Sep. 30, 2005; Date of Mailing of International Search Report Oct. 19, 2005 (2 pages).
Conway, Barbara R (2003) "Chewing gum as a drug delivery system"; Research Report;. PharmaDeals; 3 pages.

* cited by examiner

TOBACCO ALKALOID RELEASING CHEWING GUM

BACKGROUND OF THE INVENTION

Pharmaceutical use of chewing gum is well known for different purposes. One of these purposes include the use of nicotine-releasing chewing gum, typically being applied for the purpose of providing a release of nicotine in a users mouth over a certain period. A problem to be dealt with in this context is that of emulating the nicotine release and oral perception of a cigarette when it is smoked by a user.

Different ways of incorporating the nicotine into the chewing gum by mixing or initial preparation of the nicotine has been disclosed in the prior art.

One of these prior art disclosures includes U.S. Pat. No. 5,488,962 A specifically dealing with the problem of simulating the cigarette smoking with respect to the level of nicotine retention in the blood and saliva. According to the disclosure, an initial peak of nicotine level in the blood is obtained more similar to the corresponding, absorption of nicotine when smoking a cigarette. The levels reached after a certain time corresponds to conventional nicotine holding chewing gums.

A problem is, however, that the modification of the initial release typically results in a modified long-term release.

It is the object of the invention to obtain a tobacco alkaloid release corresponding to the release and absorption obtained when a user is smoking a cigarette.

SUMMARY OF THE INVENTION

The invention relates to a tobacco alkaloid releasing chewing gum comprising tobacco alkaloid, gum base, and chewing gum ingredients, said gum base comprising elastomer- and resin-compounds constituting an amount in the range of about 2 to 20% by weight of said chewing gum.

Generally, the term "tobacco alkaloid" herein refers to nicotine or nicotine substitutes.

According to the terms of the invention, the percentage of weight refers to the part(s) of the chewing gum comprising elastomer- and resin compounds, i.e. typically an uncoated chewing gum center, one or more gum base containing part(s) of a multimodular chewing gum, etc.

The term "resin compounds" includes both natural resins and synthetic resins as well as compounds referred to as "elastomer plasticizers", i.e. polymer compounds implemented as plasticizers for elastomers.

Herein the term "gum base" refers both to a separately prepared gum base mixture and to the gum base components as such. In other words, the chewing-gum may be prepared in two steps by first mixing the gum base and afterwards mixing gum base and chewing gum ingredients together, and the chewing gum may alternatively be prepared in one step, e.g. by extruding and e.g. by a one step batch process such as disclosed in WO 02/076229. In a one step process, the gum base components are added into the chewing gum, although the gum base is not mixed separately.

A chewing gum may typically, according to an embodiment of the invention, weigh in the range of 0.1 gram to 10 gram including an optional coating, although other weights may apply.

In an embodiment of the invention, said chewing gum comprises tobacco alkaloid in an amount of 0.1 mg to 10 mg.

In an embodiment of the invention, an advantageous concentration of tobacco alkaloid is within the range 0.1 mg to 10 mg per piece of chewing gum, thereby obtaining a match between the applied amount of tobacco alkaloid in the chewing gum, the desired release of tobacco alkaloid during chewing, the desired oral reception of tobacco alkaloid and acceptable textural properties.

In an embodiment of the invention, said chewing gum comprises tobacco alkaloid in an amount of 0.1 mg to 10 mg in the gum base containing part(s) of the chewing gum.

The gum base containing part of the chewing gum may typically be the chewing gum center, or core, basically forming an uncoated chewing gum piece comprising essentially the whole chewing gum composition formed from chewing gum base and further ingredients. The chewing gum center may be provided with an outer coating. In further embodiments of the invention, the gum base containing part(s) are modules, e.g. layers, of the chewing gum and may even comprise the coating.

In an embodiment of the invention, said tobacco alkaloid is in a form selected from tobacco alkaloid salts, tobacco alkaloid bound in a complex, or any combination thereof.

In an embodiment of the invention, said tobacco alkaloid is nicotine.

In an embodiment of the invention, said nicotine is in a form selected from nicotine salts, nicotine free base, nicotine bound in a complex, or any combination thereof.

In an embodiment of the invention, said complex comprises an ion exchange resin.

In an embodiment of the invention, said ion exchange resin is a weakly acidic cation exchange resin.

According to an embodiment of the invention, a preferred example of a weakly acidic cation exchange resin is polacrilex, which is described in USP 24.

In an embodiment of the invention, said complex comprises an adsorbent.

In an embodiment of the invention, said adsorbent is selected from the group consisting of finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, or any combination thereof.

In an embodiment of the invention, said nicotine salts are selected from the group comprising nicotine hydrochloride, nicotine dihydrochloride, nicotine monotartrate, nicotine bitartrate, nicotine sulfate, nicotine zinc chloride, nicotine salicylate, or any combination thereof.

In an embodiment of the invention, said chewing gum comprises emulsifiers in an amount in the range of 0.1% to 25% by weight of said chewing gum.

As referred to herein, the term "emulsifier" covers the term "solubilizer".

In an embodiment of the invention, at least 50% of said emulsifiers are comprised in said gum base.

In an embodiment of the invention, said emulsifiers are selected from the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, or any combination thereof.

In an embodiment of the invention, said chewing gum comprises one or more emulsifiers having a HLB value of 7 or less.

According to the invention, emulsifiers of HLB (hydrophilic-lipophilic balance) value below 7, or even below 5, may have advantageous softening properties, especially for softening of the gum base part of the chewing gum.

In an embodiment of the invention, said chewing gum comprises one or more emulsifiers having a HLB value of at least 7.

According to the invention, emulsifiers of HLB above about 5, preferably above about 7, have advantageous properties for increasing the release of the tobacco alkaloid. According to the invention, these relatively high-HLB-emulsifiers are preferably added at the same time in the chewing gum manufacturing process as the tobacco alkaloid.

In an embodiment of the invention, said chewing gum comprises one or more emulsifiers having an HLB value of at least 10, preferably at least 14.

In an embodiment of the invention, said chewing gum comprises one or more emulsifiers of HLB value below about 7 and one or more emulsifiers of HLB value above about 7, said emulsifiers of HLB value below about 7 being applied in the gum base, and said emulsifiers of HLB value above about 7 being applied in the final chewing gum composition along with the chewing gum ingredients.

In an embodiment of the invention, said resin-compounds comprise natural resins constituting an amount in the range of 0.1 to 20% by weight of said chewing gum.

In an embodiment of the invention, said resin-compounds comprise natural resins constituting an amount in the range of 1 to 15% by weight of said chewing gum.

In an embodiment of the invention, said natural resins comprise ester gums.

In an embodiment of the invention, said resin-compounds comprise synthetic resins constituting an amount in the range of 0.1 to 20% by weight of said chewing gum.

In an embodiment of the invention, said resin-compounds comprise synthetic resins constituting an amount in the range of 1 to 15% by weight of said chewing gum.

In an embodiment of the invention, said synthetic resins comprise terpene resins derived from alpha-pinene, beta-pinene and/or d-limonene.

In an embodiment of the invention, said synthetic resins comprise polyvinyl acetate (PVAc).

In an embodiment of the invention, said elastomer compounds comprises at least 1% by weight of said chewing gum, preferably at least 2% by weight of said chewing gum.

According to an embodiment of the invention, an advantageous amount of elastomer should be at least 1% by weight of the chewing gum, thereby obtaining a match between the applied amount of tobacco alkaloid in the chewing gum, the desired release of tobacco alkaloid during chewing, the desired oral reception of tobacco alkaloid and acceptable textural properties.

In an embodiment of the invention, said elastomer compounds constitute less than 20% by weight of said chewing gum, preferably less than about 15% by weight of said chewing gum and most preferably less than 10% by weight of said chewing gum.

According to an embodiment of the invention, the amount of elastomers should be carefully controlled in order to obtain the desired gum properties especially with respect to the initial chew of the chewing gum, as an initial high chew-resistance may counteract the resulting release of tobacco alkaloid.

In an embodiment of the invention, said elastomer compounds constitute an amount in the range of about 0.001 to 20% by weight of said chewing gum, preferably within the range of about 0.001 to 15% by weight of said chewing gum and most preferably within the range of about 0.001 to 10% by weight of said chewing gum.

In an embodiment of the invention, the amount of elastomers should be carefully controlled in order to obtain the desired gum properties, both with respect to the right chew feel and with respect to avoiding a high mount of elastomers, thereby counteracting especially the initial chewing and thereby the initial chew-invoked release of especially tobacco alkaloid.

In an embodiment of the invention, said elastomer compounds are synthetic elastomers selected from the group comprising butadiene-styrene copolymers, polyisobutadiene, isobutylene-isoprene copolymers, butyl rubber, polybutene, polybutadiene, polyisobutylene, polyvinyl acetate, polyethylene, vinyl acetate/vinyl laurate copolymer, vinyl acetate/vinyl stearate copolymer, ethylene/vinyl acetate copolymer, polyvinyl alcohol, or any derivatives or mixtures thereof.

In an embodiment of the invention, said elastomer compounds are natural elastomers selected from the group comprising natural rubber, latex, guayule, natural gums, jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang, or any combination thereof.

In an embodiment of the invention, said chewing gum comprises pH controlling components.

In an embodiment of the invention, said pH controlling components are selected from the group of sodium carbonate, sodium hydrogen carbonate, potassium carbonate, potassium hydrogen carbonate, dipotassium phosphate, potassium citrate, or any combination thereof.

In an embodiment of the invention, said pH controlling components comprise an amount in the range of 0.1% to 5% by weight of said chewing gum.

In an embodiment of the invention, said pH controlling components are implying a pH value in the range of 7.4 to 10 in the buccal cavity of a user of said chewing gum.

As a fast release of nicotine from the chewing gum is provided according to the invention, a problem arises that the user may swallow a large part of the released nicotine. The nicotine part, which is swallowed, is wasted, as it is not absorbed into the bloodstream of the user. A way of reducing this problem, according to the invention, is to raise the pH-value in the mouth to a value at which absorption of nicotine is facilitated. Thus, a raised pH-value in the mouth of the user is a very important factor, according to the invention, in order to achieve the benefits of having obtained a fast release.

In an embodiment of the invention, said fast tobacco alkaloid releasing chewing gum comprises a coating.

According to the invention, it has been experienced that the fast releasing chewing gum may offer a reduced protection of tobacco alkaloid leading to a reduced stability of tobacco alkaloid within the chewing gum. The reduced stability may be observed both with regard to escape tobacco alkaloid, e.g. nicotine from the chewing gum due to its volatility and access of oxygen to the tobacco alkaloid incorporated in the chewing gum composition. It has, however, been found, according to the invention, that a coating of the chewing gum may provide an improved protection and increased stability of the tobacco alkaloid in the chewing gum.

The improved protection is mainly implying that escape of volatile tobacco alkaloid is reduced and that access light and of oxygen from the air is reduced. By reducing the oxygen access, reactions between oxygen and nicotine are reduced, thereby maintaining tobacco alkaloid in the preferred form. Likewise, reduction of light access to the tobacco alkaloid reduces the occurrence of oxidation and further reactions of the tobacco alkaloid such as nicotine. Thus, a significant advantage obtained by applying a coating according to the invention is that a more simple and less expensive wrapping or packaging may be applied compared to the packaging, which is typically necessary for protection of chewing gum comprising a tobacco alkaloid.

In an embodiment of the invention, said coating is a hard coating.

According to the invention, especially a hard coating is providing the chewing gum with improved protective characteristics as regards protection of tobacco alkaloid within the chewing gum.

In an embodiment of the invention, said coating is a soft coating or a film coating.

Also, a soft coating and a film coating may, according to the invention, provide some contribution to the protection of tobacco alkaloid contents in the chewing gum.

In an embodiment of the invention, said coating comprises a further amount of tobacco alkaloid.

When incorporating tobacco alkaloid in the coating an initial very fast release of tobacco alkaloid may be obtained. Again, this advantage may be utilized together with the benefits of the applied amounts of resinous and elastomers, which may basically take over from the coating when the initial burst of tobacco alkaloid has been obtained and maintain a continuous release of tobacco alkaloid even after the coat is dissolved.

In an embodiment of the invention, said coating has a weight above 20 mg, preferably above 50 mg, and most preferably above 100 mg.

In experiments performed by the inventor coatings with a weight of approximately 20 mg has been successfully applied to the chewing gum center. In chewing gum with coatings of approximately 100 mg, a protective effect has been observed in keeping volatile nicotine inside the chewing gum.

The weight of the uncoated chewing gum center may be within the range of 0.4 g to 10 g.

In an embodiment of the invention, said coating make up more than 2%, preferably more than 5%, and most preferably more than 10% by weight of the chewing gum.

In an embodiment of the invention, said chewing gum comprises a coating comprising a portion of at least 100 milligrams and wherein said portion comprises high-intensity sweetener.

In an embodiment of the invention, said coating comprising a portion of at least 100 milligrams and wherein said portion comprises bulk sweetener.

In an embodiment of the invention, said coating comprising at least a portion of at least 100 milligrams and wherein said portion comprises flavor.

In an embodiment of the invention, said chewing gum comprises sweeteners.

In an embodiment of the invention, said sweeteners comprise bulk sweeteners, sugar sweeteners, sugar substitute sweeteners, artificial sweeteners, high-intensity sweeteners, or any combination thereof.

In an embodiment of the invention, said chewing gum comprises one or more flavoring agents.

In an embodiment of the invention, said flavoring agents comprise natural and synthetic flavorings.

In an embodiment of the invention, said flavoring agents comprise essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, eucalyptus, mint, or any combination thereof.

In an embodiment of the invention, said chewing gum comprises filler.

In an embodiment of the invention, said filler is comprised within said gum base.

In an embodiment of the invention, said filler is incorporated in said chewing gum along with said chewing gum ingredients.

In an embodiment of the invention, said chewing gum has a weight in the range of 0.1 to 10 grams.

In an embodiment of the invention, said chewing gum is multimodular.

In an embodiment of the invention, said chewing gum comprises a fast tobacco alkaloid releasing module, preferably a substantially gum base free module.

In an embodiment of the invention, said chewing gum is a chewing gum tablet.

Apart from being mixing in one step or two steps or extruded, the chewing gum according to the invention may also be prepared by tabletting, i.e. by compression of the chewing gum components. A chewing gum piece prepared by tabletting may be referred to as a chewing gum tablet.

In an embodiment of the invention, said chewing gum comprises further active ingredients.

Examples of further active ingredients applicable within the scope of the invention are listed in the detailed description.

According to the invention, the further active ingredients are incorporated in the chewing gum center or core of the chewing gum. Hereby, a synchronized release of tobacco alkaloid and further active ingredients may be obtained according to the invention. Thus, effects of the tobacco alkaloid may be increased or compensated in a synchronized manner.

In an embodiment of the invention, the amount of said further active ingredients is within the range of about 0.01 mg to 1000 mg, preferably in the range of 0.01 mg to 500 mg.

In an embodiment of the invention, said further active ingredients are selected from the group consisting of dental agents and agents for treating pain, headache, or weight-gain. Such active ingredients are listed in the detailed description.

In an embodiment of the invention, said further active ingredients are selected from the group consisting of cetirizine, loratidin, phenyleferin, paracetamol, cimetidin, ranitidin, ibuprofen, calciumcarbonat, vitamin D3, sumatriptan, ketoprofen, naproxen, morphine, cimetidine, famotidine, ranitidine, chlorpheneramine, dextrometorphane, metformine, or any combination thereof.

In an embodiment of the invention, said emulsifiers are selected from the group of cyclodextrins, polyoxyethylene (20) sorbitan monostearates, sorbitan fatty acid esters, glycerol polyethyleneglycol oxystearate, glycerol monostearate, glycerol monooleate, block copolymers of ethylene and propylene oxides, or mixtures thereof.

Moreover, the invention relates to a method of preparing a fast tobacco alkaloid releasing chewing gum according to any of the claims 1 to 60.

THE DRAWINGS

The invention will be described in the following with reference to the drawing, where.

DETAILED DESCRIPTION

According to the present invention, a fast tobacco alkaloid releasing chewing gum has been provided. The chewing gum has shown remarkable increased release of tobacco alkaloid such as nicotine during the first minutes of chewing.

In general, a chewing gum composition typically comprises a water-soluble bulk portion, a water-insoluble chewable gum base portion and flavoring agents. The water-soluble portion dissipates with a portion of the flavoring agent over a period of time during chewing. The gum base portion is retained in the mouth throughout the chew. The term "chewing gum" refers to both a chewing and bubble type gum in its general sense.

The gum base is the masticatory substance of the chewing gum, which imparts the chew characteristics to the final product. The gum base typically defines the release profile of flavors and sweeteners and plays a significant role in the gum product.

The insoluble portion of the gum typically may contain any combination of elastomers, vinyl polymers, elastomer plasticizers, waxes, softeners, fillers and other optional ingredients such as colorants and antioxidants.

The composition of gum base formulations can vary substantially depending on the particular product to be prepared and on the desired masticatory and other sensory characteristics of the final product. However, typical ranges (% by weight of the gum base) of the above gum base components are: 1 to 50% elastomeric compounds, 5 to 55% elastomer plasticizers, 0 to 40% waxes, 5 to 35% softeners, 0 to 50% fillers, and 0 to 5% miscellaneous ingredients such as antioxidants, colorants, etc.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

The elastomer may be any water-insoluble polymer known in the art, and includes those gum polymers utilized for chewing gum and bubble gum listed in Food and Drug Administration, CFR, Title 21, Section 172,615, as "Masticatory Substances of Natural Vegetable Origin" and "Masticatory Substances, Synthetic".

Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang.

Useful synthetic elastomers include high-molecular weight elastomers such as butadiene-styrene copolymers, polyisobutadiene and isobutylene-isoprene copolymers, low-molecular weight elastomers such as polybutene, polybutadiene and polyisobutylene, vinyl polymeric elastomers such as polyvinyl acetate, polyethylene, vinyl copolymeric elastomers such as vinyl acetate/vinyl laurate, vinyl acetate/vinyl stearate, ethylene/vinyl acetate, polyvinyl alcohol or mixtures thereof.

Butadiene-styrene type elastomers, or SBR as they may be called, typically are copolymers of from about 20:80 to 60:40 styrenes:butadiene monomers. The ratio of these monomers affects the elasticity of the SBR as evaluated by mooney viscosity. As the styrene:butadiene ratio decreases, the mooney viscosity decreases. The structure of SBR typically consists of straight chain 1,3-butadiene copolymerized with phenylethylene (styrene) and provides the non-linear molecular nature of these elastomers. The average molecular weight of SBR is <600.000 g/mole.

Isobutylene-isoprene type elastomers, or butyl as they may be called, have molar percent levels of isoprene ranging from 0.2 to 4.0. Similar to SBR, as the isoprene:isobutylene ratio decreases, so does the elasticity, measured by mooney viscosity.

The structure of butyl rubber typically consists of branched 2-methyl-1,3-butadiene (isoprene) copolymerized with branched 2-methylpropene (isobutylene), and, as with SBR, this type of structure is non-linear in nature. The average molecular weight of SBR is in the range from 150,000 g/mole to 1,000,000 g/mole.

Polyisobutylene, or PIB as they may be called, type elastomers are polymers of 2-methylpropene and, as with SBR and butyl, are non-linear in nature. The low-molecular weight elastomers provide soft chew characteristics to the gum base and still provide the elastic qualities as do the other elastomers. Average molecular weights may range from about 30,000 to 120,000 g/mole and the penetration may range from about 4 millimeters to 20 millimeters. The higher the penetration, the softer the PIB. Similar to the SBR and butyl, the high-molecular weight elastomers provide elasticity to the gum. Average molecular weight may range from 120,000 to 1,000,000 g/mole.

Polybutenes range in average molecular weight from about 5,000 g/mole to about 30,000 g/mole.

Vinyl polymeric and copolymeric type elastomers provide tack resistance, vary the chew characteristics of gums made from these bases having vinyl polymers and offer hydrophilic properties beneficial to sensory perception of the final gums.

For vinyl copolymeric types, the amount of vinyl laurate, vinyl stearate, or ethylene present in the vinyl laurate/vinyl acetate (VLNA), vinyl stearate/vinyl acetate (VS/VA), or ethylene/vinyl acetate (EVA) copolymers respectively typically ranges from about 10 to about 60% by weight of the copolymer. Average molecular weights of these polymers may range from about 2,000 g/mole to about 100,000 g/mole.

The vinyl polymers such as polyvinyl alcohol and polyvinyl acetate have an average molecular weight from about 8,000 g/mole to about 65,000 g/mole.

Polymers of vinyl acetate (PVAc) are branched in nature. The degree of branching is increased when vinyl acetate monomers are copolymerized with vinyl laurate, vinyl stearate, ethylene and the like. The higher the degree of branching, the higher the compatibility when blended or compounded with normal-alkanic and iso-alkanic type waxes.

It is e.g. common in the industry to combine in a gum base a synthetic elastomer having a high-molecular weight and a low-molecular-weight elastomer. Presently preferred combinations of synthetic elastomers include, but are not limited to, polyisobutylene and styrene-butadiene, polyisobutylene and polyisoprene, polyisobutylene and isobutylene-isoprene copolymer (butyl rubber) and a combination of polyisobutylene, styrene-butadiene copolymer and isobutylene isoprene copolymer, and all of the above individual synthetic polymers in admixture with polyvinyl acetate, vinyl acetate-vinyl laurate copolymers, respectively and mixtures thereof.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkanic chains of the waxes.

Elastomer plasticizers suitable for use in the present invention include natural rosin esters often referred to as ester gums. Such elastomer plasticizers known in the art are methyl, glycerol and pentaerythritol esters of rosins and modified rosins, such as hydrogenated, dimerized and polymerized rosins. Examples are glycerol ester of wood and gum rosin, glycerol ester of partially hydrogenated wood and gum rosin, glycerol ester of polymerized wood and gum rosin, glycerol ester of partially dimerized wood and gum rosin, glycerol ester of tall oil rosin, pentaerythritol ester of wood and gum rosin, pentaerythritol esters of partially and fully hydrogenated wood and gum rosin, methyl esters of wood and gum rosins and partially and fully hydrogenated methyl esters of wood and gum rosin.

The synthetic elastomer plasticizers include terpene resins derived from alpha-pinene, beta-pinene and/or d-limonene.

The elastomer plasticizers used may be of one type or of combinations of more than one type. Typically, the ratios of one to the other are dependent on each respective softening point, the effect on flavor release, and the respective degree of tack they cause to the gum. Ball and ring softening points of the rosin ester types described above may range from about 45° C. to about 120° C. Softening points of the terpene resins may range from about 60° C. to about 130° C.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes. The compatibility of gum bases made using normal-alkanic waxes is less when compared to gum bases made with iso-alkanic waxes.

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths >C-18 but the lengths are not predominantly longer than C-30. The branched and ring structures are located near the end of the chain for those waxes that are predominantly normal-alkanic. The viscosity of normal-alkanic waxes is <10 mm2/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm2/s (at 100° C.) and the combined number average molecular weight is >600 g/mole.

Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

The natural waxes may include rice bran wax, bees' wax, carnauba wax or candelilla wax. The waxes may be used alone or in any combination.

The selection of softeners has an influence on the softness of the base. Softeners modify the texture, cause the hydrophobic and hydrophilic components of the base to be miscible, and may further plasticize the synthetic elastomers of the gum base. The emulsifiers, which belong to the group of softeners, provide the gum base with water-binding properties, which confer to the gum base a pleasant smooth surface and reduce its adhesive properties.

Softeners suitable for use in the gum base include triglycerides of non-hydrogenated, partially hydrogenated and fully hydrogenated vegetable oils and tallow, cocoa butter and degreased cocoa powder and in addition to these the emulsifiers.

The group of triglycerides include cottonseed, palm, palm kernel, coconut, safflower, rapeseed, sunflower, tallow, soybean, cocoa butter, medium-chained triglycerides and the like.

The caproic, caprylic, capric, myristic, lauric and palmitic fatty acids of the triglycerides tend to plasticize the synthetic elastomers more than triglycerides containing predominantly stearic fatty acid.

To the group of emulsifiers belong the monoglycerides, diglycerides, acetylated mono and diglycerides, distilled mono- and diglycerides, glycerol monostearate, propylene glycol monostearate, Na-, K-, Mg- and Ca-stearates, glycerol triacetate, fatty acid monoglycerides (e.g. stearic, palmitic, oleic and linoleic acids), lactic acid esters and acetic acid esters of mono- and diglycerides, sugar esters of edible fatty acids also referred to as sucrose polyesters including those disclosed in WO 00/25598, lecithin and hydroxylated lecithin, most of these may contain triglyceride levels less than 2% by weight from their manufacturing processing.

The softeners including the emulsifiers may be used alone or at least two or more in combination.

Fillers used in gum base modify the texture of the gum base and aid in processing. Particle size has an effect on cohesiveness, density and processing characteristics of the gum base and its compounding. The smaller the particle size, the more dense and cohesive the final gum base. Also, by selecting fillers based on their particle size distribution, initial mass compounding may be varied, thus allowing alteration of the compounding characteristics of the initial mass during gum base processing and ultimately the final chew characteristics of gums made from these gum bases.

Fillers suitable for use in the gum base include magnesium and calcium carbonate, ground limestone and silicate types such as magnesium and aluminum silicate, kaolin and clay, aluminum oxide, silicium oxide, talc, as well as titanium oxide, mono-, di- and tricalcium phosphate, sodium sulphate, cellulose polymers such as ethyl, methyl and wood or mixtures thereof.

Talc filler may be used in the gum base and gum of the present invention that may come in contact with or employ acid flavors or provide an acidic environment needed to prevent degradation of an artificial sweetener by reacting with calcium carbonate type fillers. Mean particle size for calcium carbonate and talc fillers typically range from about 0.1 micron to about 15 microns.

The fillers may also include natural organic fibers such as fruit vegetable fibers, grain, rice, cellulose and combinations thereof.

Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

Flavorants and colorants impart characteristics or remove or mask undesired characteristics. Colorants may typically include FD&C type lakes, plant extracts, fruit and vegetable extracts and titanium dioxide flavorants may typically include cocoa powder, heat-modified amino acids and other vegetable extracts.

Gum bases are typically prepared by adding an amount of the elastomer, elastomer plasticizer and filler, and on occasion a vinyl polymer, to a heated (10° C.-120° C.) sigma blade mixer with a front to rear speed ratio of from about 1.2:1 to about 2:1, the higher ratio typically being used for gum base which requires more rigorous compounding of its elastomers.

The initial amounts of ingredients comprising the initial mass may be determined by the working capacity of the mixing kettle in order to attain a proper consistency and by the degree of compounding desired to break down the elastomer and increase chain branching. The higher the level of filler at the start or selection of a filler having a certain particle size distribution, the higher the degree of compounding and thus more of the elastomeric chain crosslinking are broken, causing more branching of the elastomer thus lower viscosity gum bases and thus softer final gum base and gum made from such a gum base. The longer the time of compounding, the use of lower molecular weight or softening point gum base ingredients, the lower the viscosity and firmness of the final gum base.

Compounding typically begins to be effective once the ingredients have massed together. Anywhere from 15 minutes to 90 minutes may be the length of compounding time.

Preferably, the time of compounding is from 20 minutes to about 60 minutes. The amount of added elastomer plasticizer depends on the level of elastomer and filler present. If too much elastomer plasticizer is added, the initial mass becomes over plasticized and not homogeneous.

After the initial ingredients have massed homogeneously and compounded for the time desired, the balance of the gum base ingredients are added in a sequential manner until a completely homogeneous molten mass is attained. Typically, any remainder of elastomer, elastomer plasticizer, vinyl polymer and filler, are added within 60 minutes after the initial compounding time. The filler and the elastomer plasticizer would typically be individually weighed and added in portions during this time. The optional waxes and the softeners are typically added after the elastomer and elastomer plasticizers and during the next 60 minutes. Then the mass is allowed to become homogeneous before dumping.

Typical gum base processing times may vary from about one to about three hours, preferably from about 1½ to 1½ hours, depending on the formulation. The final mass temperature when dumped may be between 70° C. and 130° C. and preferably between 100° C. and 120° C. The completed molten mass is emptied from the mixing kettle into coated or lined pans, extruded or cast into any desirable shape and allowed to cool and solidify. Those skilled in the art will recognize that many variations of the above-described procedure may be followed.

The water-soluble portion of the chewing gum may comprise chewing gum ingredients such as softeners, sweeteners, high-intensity sweeteners, flavoring agents, acidulants, fillers, antioxidants, and other components that provide desired attributes. Softeners typically constitute from about 0.5% to about 25.0% by weight of the chewing gum. The bulking agents generally comprise from about 5% to about 90%, preferably from about 20% to about 80% of the chewing gum. High-intensity sweeteners in gum typically may range from about 0.01 to 0.50 weight percent. A flavoring agent may be present in the chewing gum in an amount within the range of from about 0.1 to about 30.0 weight percent of the gum.

According to the present invention, the term "tobacco alkaloid" includes both nicotine and nicotine-like alkaloids and may be in free base form or any pharmacologically acceptable acid addition salt form.

According to the invention, nicotine or other tobacco alkaloids may be applied in a chewing gum from which they are rapidly released during chewing. The term "nicotine" includes diprotonated nicotine, monoprotonated nicotine as well as nicotin free base. Further tobacco alkaloids, which may substitute nicotine, include such compounds as cotinine, norcotile, nornicotine, lobeline, derivatives of lobeline, nicotine N-oxide, cotinine N-oxide, 3-hydroxycotile, 5-hydroxycotile, derivatives of epibatidine, N-methylcarbamyl, N-methylthi-O-carbamyl esters of choline, acetylcholine, and etc.

Preferred nicotine substitutes according to the invention include plant alkaoids obtainable from species of *Nicotiana*, which is a source for nicotine and nor-nicotine, as well as species of *Lobelia* and Lobeliaceae (Indian tobacco), which are a source for lobeline.

The tobacco alkaloid, i.e. nicotine or the substitutes therefore may preferably be added into the chewing gum at the stage of mixing the chewing gum ingredients with the gum base. It is, however, within the scope of the invention to mix nicotine into the gum base. The nicotine is preferably substantially uniformly distributed in the chewing gum or in a part of the chewing gum.

The amount of nicotine or other tobacco alkaloids added into the chewing gum may, according to the invention, be within the range of 0.1 mg to 10 mg, preferably 0.5 mg to 5 mg, and most preferably 1 mg to 4 mg. Typical doses of 2 mg and 4 mg nicotine in a nicotine chewing gum may also be applied in embodiments of the present invention.

According to a preferred embodiment of the invention, nicotine may be applied as the tobacco alkaloid. Nicotine may be added in a free base form, but preferably nicotine is bound as a salt and/or in a complex prior to addition into the chewing gum mixture. Both absorption and adsorption may be suitable ways of binding nicotine to a suitable complex or compound.

In a nicotine-containing complex, nicotine may be bound to a cation exchange resin. The cation exchanging groups may be strongly acidic, intermediately acidic, or weakly acidic, depending on the acid from which the functional groups are derived. Examples of suitable acidic groups include carboxylic, sulphonic, phosphonous, phosphoric, iminodiacetic, and phenolic acid. If the ion exchange resin further comprises anionic groups, a polyampholyte may be obtained, and by using a suitable mixture of counter-ions, the release characteristics may be varied.

The ion exchange resins according to the invention comprise acidic ions, which are bound to a polymer such as a crosslinked or a linear polymer. Examples include addition polymers of styrene and divinylbenzene, divinylbenzene and methacrylic acid or acrylic acid, phenolic resins, cellulose, and etc.

Further details about applicable ion exchange resins are outlined in U.S. Pat. No. 3,845,217 and U.S. Pat. No. 3,901, 248, hereby incorporated by reference.

A preferred complex for binding nicotine before addition into the chewing gum is a weakly acidic cation exchange resin such as polacrilex according to USP 24 United States Pharmacopeia no. 24), which is available as Amberlite IRP 64.

Further suitable alternative complexes, which may be applied according to the present invention are adsorbent complexes, wherein nicotine or another alkaloid is bound to or sorbed on an adsorbent such as finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, and the like. Further details about adsorbents for nicotine are outlined in U.S. Pat. No. 3,877,468 and WO2004/056363, hereby incorporated by reference.

According to a further embodiment of the invention, different tobacco alkaloids are applied in the chewing gum at the same time, and may even be bound in the same complex, such as in the above-mentioned adsorbents or ion exchange resins.

According to an embodiment of the invention, nicotine is a preferred tobacco alkaloid for application in the fast releasing chewing gum of the invention. Thus, it should generally be noted that nicotine is a preferred tobacco alkaloid. However, it should further be noted that specific examples and explanations specifically referring to nicotine as active agent against craving in no way restrict the scope of the invention with respect to use of other tobacco alkaloids for the same specific purpose. A specific mentioning of nicotine at any place in this application is only used for the purpose of exemplifying the invention in a tangible way and not for the purpose of excluding alternative functional equivalents.

Furthermore, according to the present invention, the term "nicotine" may encompass nicotine or nicotine derivatives in any form such as, e.g. physical forms like amorphous, crystalline, polymorphous, etc. or chemical forms like isomers and enantiomers, etc. as well as any pharmaceutically acceptable salts, complex or solvate thereof. Nicotine may be selected from nicotine base, nicotine hydrochloride, nicotine dihydrochloride, nicotine monotartrate, nicotine bitartrate, nicotine sulfate, nicotine zinc chloride such as zinc chloride monohydrate and nicotine salicylate.

Softeners are added to the chewing gum in order to optimize the chewability and mouth feel of the gum.

Softeners contemplated for use in the gum include glycerin, modified lecithin and combinations thereof. Further aqueous sweetener solutions such as those containing sorbitol, hydrogenated starch hydrolysates, corn syrup and combinations thereof may be used as softeners.

Bulk sweeteners include both sugar and sugarless components. Bulk sweeteners may typically constitute 5 to about 95% by weight of the chewing gum, more typically constitute 20 to about 80% by weight, and more commonly, 30 to 60% by weight of the gum.

The sweeteners often fill the role of bulking agents in the gum. The sweeteners are improving juiciness of the gum and are supporting the flavor profile of the gum. Sugar sweeteners generally include, but are not limited to saccharide-containing components commonly known in the chewing gum art, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination.

The sweetener can be used in combination with sugarless sweeteners. Generally, sugarless sweeteners include components with sweetening characteristics but which are devoid of the commonly known sugars and comprise, but are not limited to, sugar alcohols such as sorbitol, mannitol, xylitol, hydrogenated starch hydrolyzates, maltitol, isomalt, erydiritol, lactitol and the like, alone or in combination.

Depending on the particular sweetness release profile and shelf life stability needed, bulk sweeteners can also be used in combination high-intensity sweeteners. Preferred high-intensity sweeteners include, but are not limited to sucralose, aspartame, salts of acesulfame, alitame, saccharin and its salts, cyclamic acid and its salts, cyclamate, glycyrrhizin, dihydrochalcones, thaumatin, monellin, sterioside and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coascervation, encapsulation in yeast cells and fiber extrusion may be used to achieve the desired release characteristics. The encapsulation can also be performed in another material such as resin.

Usage level of the artificial sweetener will vary greatly and will depend on such factors as potency of the sweetener, rate of release, desired sweetness of the product, level and type of flavor used and cost considerations. Thus, the active level of artificial sweetener may vary from 0.02 to about 8%. When carriers used for encapsulation are included, the usage level of the encapsulated sweetener will be proportionally higher. Combinations of sugar and/or sugarless sweeteners may be used in chewing gum.

Additionally, the softener may also provide additional sweetness, if such softeners as aqueous sugar or alditol are used.

If a low-calorie gum is desired, a low-caloric bulking agent can be used. Examples of low-caloric bulking agents include polydextrose; Raftilose, Raftilin; Fructooligo-saccharides (NutraFlora®); Palatinose oligosaccharide; Guar Gum Hydrolysate (SunFiber®); or indigestible dextrin (Fibersol). However, other low-caloric bulking agents can be used.

The chewing gum centers provided herein may contain aroma agents and flavoring agents including natural and synthetic flavorings e.g. in the form of natural vegetable components, essential oils, essences, extracts, powders, including acids and other substances capable of affecting the taste profile. Examples of liquid and powdered flavorings include coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits (e.g. lemon, bergamot and orange) as mentioned above.

The chewing gum flavor may be a natural flavoring agent, which is freeze-dried, preferably in the form of a powder, slices or pieces of combinations thereof. The particle size may be less than 3 mm, preferably less than 2 mm, more preferably less than 1 mm, calculated as the longest dimension of the particle. The natural flavoring agent may be in a form where the particle size is from about 3 µm to 2 mm, such as from 4 µm to 1 mm. Preferred natural flavoring agents include seeds from a fruit e.g. from strawberry, blackberry and raspberry.

Various synthetic flavors, such as mixed fruit flavors may also be used in the present chewing gum centers. The aroma agent may be used in quantities smaller than those conventionally used. The aroma agents and/or flavors may be used in an amount of from 0.01 to about 30% by weight (preferably from 0.01 to about 15% by weight) of the final product depending on the desired intensity of the aroma and/or flavor used. Preferably, the content of aroma/flavor is in the range of from 0.2 to 3% by weight of the total composition.

Also various acids are used typically in combination with fruit flavors, such as adipinic acid, succinic acid, fumaric acid, citric acid, tartaric acid, malic acid, acetic acid, lactic acid, phosphoric acid and glutaric acid or salts thereof. They are typically added in amounts of 0.01 to 10%.

The chewing gum may also comprise the following surfactants and/or solubilizers, especially when active ingredients are present. As examples of types of surfactants to be used as solubilizers in a chewing gum composition according to the invention reference is made to H. P. Fiedler, Lexikon der Hilfstoffe fur Pharmacie, Kosmetik und Angrenzende Gebiete, page 63-64 (1981) and the lists of approved food emulsifiers of the individual countries. The solubilizers referred to herein are also recognized by the term "emulsifiers".

Both anionic, cationic, amphoteric, and nonionic solubilizers can be used, but usually the solubilizer, i.e. emulsifier used is either anionic or nonionic as mainly such solubilizers are approved for use in food or medicines. In cases where the active agent is reactive it is usually an advantage to use a nonionic solubilizer as it is not very reactive and therefore does not affect the stability of the active agent unfavorably.

Suitable solubilizers include lecithines, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids, which solubilizers are all known for use as food emulsifiers, and polyoxyethylated hydrogenated castor oil (for instance such sold under the trade name CREMOPHOR), block copolymers of ethylene oxide and propylene oxide (for instance as sold under the trade name PLURONIC or the trade name POLOXAMER), polyoxyethylene fatty alcohol ethers, polyoxyethylene sorbitan fatty acid esters, sorbitan esters of fatty acids and polyoxyethylene steraric acid ester, all known in the EEC for use as pharmaceutical-cosmetical emulsifiers.

Further examples of applicable solubilizers are polyoxyethylene stearates, such as for instance polyoxyethylene (8) stearate and polyoxyethylene (40) stearate, the olyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, block copolymers of ethylene oxide and propyleneoxide and polyoxyethylene fatty alcohol ether. The solubilizer may either be a single compound or a combination of several compounds. The expression "solubilizer" is used in the present text to describe both possibilities, the solubilizer used must be suitable for use in food and/or medicine.

Preferred solubilizers according to the invention include Atmos 300 NL, Cremophor EL, Cremophor A6, Lecithin, Modified lecithin, Poloxamer 188, Poloxamer 124, Poloxamer 237, Poloxamer 338, Polyoxyl 10 oleyl ether, Polyoxyl 20 cetostearyl ether, Polyethylene glycol, Polysorbate 20, Polysorbate 80, Polyoxyl 40 stearate, Polyoxyl 50 stearate, RS-5540, Sodium lauryl sulphate, Sorbitan monolaurate, Panodan 165, Lactodan B30, Dimodan PV, Artodan SP55, and Triodan R90. The most preferred solubilizers according to the invention include cyclodextrins, Cremophor RH40, Poloxamer 407, Polysorbate 60, Glyceryl monooleate, Glyceryl monostearate, Sorbitan monooleate, Sorbitan monopalmitate, Sorbitan monostearate, Sorbitan sesquioleate, and Sorbitan trioleate.

According to the invention, a chewing gum is provided which releases tobacco alkaloid such as nicotine quickly when chewed by a user of the chewing gum. In order to obtain the effect of the considerably large amount of nicotine released at once, it is important that conditions for absorbing a large amount of the nicotine are provided as well. Otherwise, an undesirable large part of the fast releasing nicotine may be wasted, e.g. by being swallowed by the user. According to the invention, the increase in absorption of nicotine into the capillary blood and bloodstream of the user may be obtained by way of adding components for adjusting pH. Such components may be referred to as buffering agents and may be applied for raising the pH above the normal human mouth pH in the saliva of the user. Hereby, nicotine is to a larger extent converted from ionized nicotine to unionized nicotine, which is more readily crossing the buccal mucosa of the user. Thus, the absorption of nicotine into the bloodstream directly from the buccal cavity is increased and the part of wasted nicotine is reduced.

Components for adjusting pH include ion exchange resins and further components such as buffer agents. Buffer agents may be applied in the chewing gum in an amount in the range of 0.1% to 10%, preferably 0.5% to 5% by weight of the chewing gum. While chewing a chewing gum according to the invention, the pH in the saliva may hereby be raised to a value within the range of 7.5 to 10, preferably in the range of 8 to 9.5. It should be noted that a too large pH, such as about 9.5 to 10, might cause a relatively unpleasant soap-like experience by the user of the chewing gum. According to the invention, it is important to keep the pH at an elevated level during the first 1 to 15 minutes, especially the first 1 to 10 minutes, as nicotine is quickly released during this period of chewing. According to a preferred embodiment of the invention, more than half of the nicotine-content of the chewing gum may be released from the chewing gum within the first 5 minutes.

Examples of components for adjusting the pH in the oral cavity include for instance: acceptable acids, such as adipinic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

According to the invention, preferred buffers for adjusting pH include sodium-carbonate, sodium hydrogen carbonate, potassium carbonate, potassium hydrogen carbonate, disodium hydrogen phosphate, dipotassium hydrogen phosphate, dipotassium phosphate, trisodium phosphate, tripotassium phosphate, calcium hydroxide, magnesium oxide, potassium citrate, sodium glycinate, and combinations thereof. The most preferred buffer agents according to the invention are alkali metal carbonates and phospates.

Fillers suitable for use in the chewing gum include magnesium and calcium carbonate, ground limestone and silicate types such as magnesium and aluminum silicate, kaolin and clay, aluminum oxide, silicium oxide, talc, as well as titanium oxide, mono-, di- and tricalcium phosphate, sodium sulphate, cellulose polymers such as ethyl, methyl and wood or mixtures thereof.

Talc filler may be used in the chewing gum of the present invention that may come in contact with or employ acid flavors or provide an acidic environment needed to prevent degradation of an artificial sweetener by reacting with calcium carbonate type fillers. Mean particle size for calcium carbonate and talc fillers typically range from about 0.1 micron to about 15 microns.

The fillers may also include natural organic fibers such as fruit vegetable fibers, grain, rice, cellulose and combinations thereof.

Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

Colorants and whiteners may include FD & C-type dyes and lakes, fruit and vegetable extracts, titanium dioxide, and combinations thereof.

The taste-masking agent improves the organoleptic properties of the product. The masking agents include sucralose, zinc gluconate, ethyl maltol, glycine, acesulfame-K, aspartame, saccharin, fructose, xylitol, spray dried licorice root, glycerrhizine, dextrose, sodium gluconate, glucono delta-lactone, ethyl vanillin, vanillin, normal and high-potency sweeteners, and a variety of appropriate flavors.

The chewing gum according to the present invention may also comprise active agents other than nicotine. Active agents to be used in connection with the present invention may be any substance desired to be released from the chewing gum. If an accelerated rate of release is desired, corresponding to the effect obtained for the flavor, the primary substances are those with limited water solubility, typically below 10 g/100 ml including substances, which are entirely water insoluble. Examples are medicines, dietary supplements, oral compositions, anti-smoking agents, highly potent sweeteners, pH adjusting agents, etc.

Further examples of active ingredients include paracetamol, benzocaine, cinnarizine, menthol, carvone, caffeine, chlorhexidine-di-acetate, cyclizine hydrochloride, 1,8-cineol, nandrolone, miconazole, mystatine, aspartame, sodium fluoride, nicotine, saccharin, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogencarbonate, the active components from ginkgo, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutrients accepted by the authorities in different countries such as for instance US code of Federal Regulations, Title 21, Section 182.5013.1825997 and 182.8013-182.8997.

Examples of active agents in the form of compounds for the care or treatment of the oral cavity and the teeth are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulfate AIK (S04) 2, 12H20) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodium-monofluorophosphate, aminofluorides, stannous fluoride), phosphates, carbonates and selenium.

Cf. furthermore J. Dent. Res. Vol. 28 No. 2, pages 160-171, 1949, wherein a wide range of tested compounds are mentioned.

Examples of active agents in the form of agents adjusting the pH in the oral cavity include for instance: acceptable acids, such as adipinic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocinelactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., Nov. 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodomase, dextranase, alpha amylase), polypeptides (oxytocin, gonadorelin, (LH. RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen, Sildenafil citrate and derivatives thereof.

Dental products include Carbamide, CPP Caseine Phospho Peptide; Chlorhexidine, Chlorhexidine di-acetate, Chlorhexidine Chloride, Chlorhexidine digluconate, Hexetedine, Strontium chloride, Potassium Chloride, Sodium bicarbonate, Sodium carbonate, Fluor containing ingredients, Fluorides, Sodium fluoride, Aluminum fluoride, Ammonium fluoride, Calcium fluoride, Stannous fluoride, Other fluor containing ingredients Ammonium fluorosilicate, Potasium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride, Vitamins include A, B1, B2, B6, B12, Folin acid, niacin, Pantothensyre, biotine, C, D, E, K.

Minerals include Calcium, phosphorus, magnesium, iron, Zinc, Copper, Iodine, Manganese, Cromium, Selenium, Molybdenum. Other active ingredients include: Q10@, enzymes. Natural drugs including *Ginkgo Biloba*, ginger, and fish oil. The invention also relates to use of migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid.

In general, chewing gum may be manufactured by sequentially adding the various chewing gum ingredients to a commercially available mixer known in the art. After the initial ingredients have been thoroughly mixed, the gum mass is discharged from the mixer and shaped into the desired form such as by rolling into sheets and cutting into sticks, extruded into chunks or casting into pellets.

Generally, the ingredients may be mixed by first melting the gum base and adding it to the running mixer. Colors, active agents and/or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor has been added.

The entire mixing procedure typically takes from five to fifteen minutes, but longer mixing times may sometimes be required. Those skilled in the art will recognize that many variations of the above-described procedure may be followed. Including the one-step method described in US patent application 2004/0115305 hereby incorporated as reference.

According to the invention, the form and shape of the tobacco alkaloid chewing gum may be any suitable and user-friendly structure. Accordingly, the gum center or gum may be e.g. in a form selected from a pellet, a cushion-shaped pellet, a stick, a tablet, a chunk, a pastille, a pill, a ball and a sphere. Chewing gums are formed by extrusion, compression, rolling and may be center filled with liquids and/or solids in any form.

In accordance with the invention, the chewing gum element may comprise about 0.1 to about 75% by weight of an outer coating applied onto the chewing gum center. Thus, suitable coating types include hard coatings, film coatings and soft coatings of any composition including those currently used in coating of chewing gum, pharmaceutical products and confectioneries and any combination thereof.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the user and it may moreover protect the gum centers for various reasons. In a typical process of providing the chewing gum centers with a protective sugar coating, the gum centers are successively treated in suitable coating equipment with aqueous solutions of crystallisable sugar such as sucrose or dextrose, which, depending on the stage of coating reached, may contain other functional ingredients, e.g. fillers, binding agents, colors, etc. In the present context, the sugar coating may contain further functional or active compounds including flavor compounds and/or pharmaceutically active compounds.

In the production of chewing gum it may, however, be preferred to replace the cardiogenic sugar compounds in the coating by other, preferably crystallisable, sweetening compounds that do not have a cariogenic effect. In the art such coating are generally referred to as sugarless or sugar-free coatings. Presently preferred non-cariogenic hard coating substances include polyols, e.g. sorbitol, maltitol, mannitol, xylitol, erythritol, lactitol, isomalt and tagatose which are obtained by industrial methods by hydrogenation of D-glucose, maltose, fructose or levulose, xylose, erythrose, lactose, isomaltulose and D-galactose, respectively and trehalose, which is a non-cariogene mono-di-saccharide.

In a typical hard coating process, as it will be described in details in the following, a suspension containing crystallisable sugar and/or polyol is applied onto the gum centers and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished chewing gum element, such as about 10 to about 60% by weight, including about 15 to about 50% by weight.

In further useful embodiments, the outer coating of the chewing gum element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to a chewing gum center of any of the above forms. The thickness of such a coating is usually between 20 and 100 μm. Generally, the film coating is obtained by passing the chewing gum centers through a spray zone with atomized droplets of the coating materials in a suitable aqueous or organic solvent vehicle, after which the material adhering to the gum centers is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers, also referred to as functional polymers are polymers that, in addition to its film-forming characteristics, confer a modified release performance with respect to active components of the chewing gum formulation. Such release modifying polymers include methylacrylate ester copolymers, ethylcellulose (EC) and enteric polymers designed to resist the acidic stomach environment, yet dissolve readily in the duodenum. The latter group of polymers includes: cellulose acetate phtalate (CAP), polyvinyl acetate phtalate (PVAP), shellac, metacrylic acid copolymers, cellulose acetate trimellitate (CAT) and HPMC. It will be appreciated that the outer film coating according to the present invention may comprise any combination of the above film-coating polymers.

In other embodiments, the film-coating layer of the chewing gum elements according to the invention comprises a plasticizing agent having the capacity to alter the physical properties of a polymer to render it more useful in performing its function as a film-forming material. In general, the effect of plasticizers will be to make the polymer softer and more pliable as the plasticizer molecules interpose themselves between the individual polymer strands thus breaking down polymer-polymer interactions. Most plasticizers used in film coating are either amorphous or have very little crystallinity. In the present context, suitable plasticizers include polyols such as glycerol, propylene glycol, polyethylene glycol, e.g. the 200-6000 grades hereof, organic esters such as phtalate esters, dibutyl sebacate, citrate esters and thiacetin, oils/glycerides including castor oil, acetylated monoglycerides and fractionated coconut oil.

The choice of film-forming polymer(s) and plasticizing agent(s) for the outer coating of the present chewing gum element is made with due consideration for achieving the best possible barrier properties of the coating in respect of dissolution and diffusion across the film of moisture and gasses.

The film coating of the chewing gum elements may also contain one or more colorants or opacifiers. In addition to providing a desired color hue, such agents may reflect light or form a barrier against moisture and gasses. Suitable colorants/pacifiers include organic dyes and their lakes, inorganic coloring agents, e.g. titanium oxide and natural colors such as e.g. β-carotene or chlorophyll.

Additionally, film coatings may contain one or several auxiliary substances such as flavors and waxes or saccharide compounds such as polydextrose, dextrins including maltodextrin, lactose, modified starch, a protein such as gelatine or zein, a vegetable gum and any combination thereof.

In one specific embodiment the chewing gum center is in the form of a stick which is provided on at least one side with an edible film comprising layer of a coating of a film forming agent, e.g. a cellulose derivative, a modified starch, shellac, gum arabic, a dextrin, gelatine, zein, a vegetable gum, a synthetic polymer and any combination thereof, and a wax such as beeswax, carnauba wax, microcrystalline wax, paraffin wax and combinations thereof.

The following examples are given for illustration, but not limitation of the invention.

Example 1

Preparation of Gum Base

A gum base is prepared, which comprises the following ingredients.

| Ingredients | Percent by weight |
| --- | --- |
| Elastomer | 10 |
| Natural resin | 28 |
| Synthetic resin | 22 |
| Fat/wax/emulsifiers | 23 |
| Fillers | 17 |

It should be emphasized that several other gum base compositions may be applied within the scope of the invention.

The elastomer and filler are added to a mixing kettle provided with mixing means like e.g. horizontally placed Z-shaped arms. The kettle has been preheated for 15 minutes to a temperature of about 120° C. The rubber is broken into small pieces and softened with mechanical action in the kettle.

The resin is slowly added to the elastomer until the mixture becomes homogeneous. The remaining resin is then added to the kettle and mixed for 10-20 minutes. The softening ingredients are added and mixed for 20-40 minutes until the whole mixture becomes homogeneous.

The mixture is then discharged into the pan and allowed to cool to room temperature from the discharged temperature of 120° C.

Example 2

Preparation of Nicotine-Containing Chewing Gum

Chewing gum is prepared by use of the gum base in example 1 and according to a conventional mechanical mixing procedure during moderate use of heating as described below.

| | |
| --- | --- |
| Gum base | 57.4% |
| Filler | 14.6% |
| Nicotine Polacrilex | |
| Nicotine | 0.2% |
| Ion exchange resin | 0.8% |
| Buffer agents | |
| Sodiumhydrogencarbonate | 1.0% |
| Sodium carbonate | 2.0% |
| Sorbitol powder | 14.4% |
| Liquid sweetener | 1.5% |
| Intense sweetener | 0.4% |
| Flavor | 7.7% |

Gum base and filler are mixed in a mixing kettle provided with mixing means like e.g. horizontally placed Z-shaped arms. The kettle has been preheated to a temperature of up to approximately 50° C.

When the content is homogenous the other ingredient is added according to a specified time schedule. Nicotine is added in the first half of the mixing process and can be added as pure nicotine, as a nicotine salt or bound to an ion exchange resin, e.g. Amberlite IRP 64.

The pieces may be formulated with 0.1-8 mg of nicotine per piece preferably 2 or 4 mg. The pieces evaluated below comprise 2 mg nicotine complex.

Example 3

Chewing gum is prepared by use of the gum base in example 1 and according to a conventional mechanical mixing procedure during moderate use of heating according to the procedure explained and described in connection with example 2.

| | |
| --- | --- |
| Gum base | 43.9% |
| Filler | 11.1% |
| Nicotine Polacrilex | |
| Nicotine | 0.2% |
| Ion exchange resin | 0.8% |
| Buffer agents | |
| Sodiumhydrogencarbonate | 1.0% |
| Sodium carbonate | 2.0% |
| Sorbitol powder | 31.4% |
| Liquid sweetener | 1.5% |
| Intense sweetener | 0.4% |
| Flavor | 7.7% |

Example 4

Chewing gum is prepared by use of the gum base in example 1 and according to a conventional mechanical mixing procedure during moderate use of heating according to the procedure explained and described in connection with example 2.

| Gum base | 31.9% |
|---|---|
| Filler | 8.1% |
| Nicotine Polacrilex | |
| Nicotine | 0.2% |
| Ion exchange resin | 0.8% |
| Buffer agents | |
| Sodiumhydrogencarbonate | 1.0% |
| Sodium carbonate | 2.0% |
| Sorbitol powder | 46.4% |
| Liquid sweetener | 1.5% |
| Intense sweetener | 0.4% |
| Flavor | 7.7% |

Example 5

Chewing gum is prepared by use of the gum base in example 1 and according to a conventional mechanical mixing procedure during moderate use of heating according to the procedure explained and described in connection with example 2.

| Gum base | 23.9% |
|---|---|
| Filler | 6.1% |
| Nicotine Polacrilex | |
| Nicotine | 0.2% |
| Ion exchange resin | 0.8% |
| Buffer agents | |
| Sodiumhydrogencarbonate | 1.0% |
| Sodium carbonate | 2.0% |
| Sorbitol powder | 56.4% |
| Liquid sweetener | 1.5% |
| Intense sweetener | 0.4% |
| Flavor | 7.7% |

Examples 6-9

The chewing gums of examples 2-5 were coated by means of hard coating. Coating was applied.

Coating may e.g. be applied according to the methods disclosed in U.S. Pat. No. 6,627,234, hereby included by reference.

Example 10

Evaluation of Release and Taste Masking of Chewing Gum of Examples 2-5

The below table 1 illustrates nicotine release of the chewing gums of examples 2-5.

TABLE 1

Nicotine release in percentage of the full amount of nicotine contained in the chewing gum.

| Chewing gum according to example | % in chewing gum of elastomer- and resin | % RELEASE at minutes | | | |
|---|---|---|---|---|---|
| | | 5 min | 10 min | 20 min | 30 min |
| Ex. 2 | 34.4 | 23 | 50 | 73 | 86 |
| Ex. 3 | 26.3 | 32 | 59 | 78 | 88 |
| Ex. 4 | 19.1 | 59 | 77 | 87 | 94 |
| Ex. 5 | 14.3 | 64 | 80 | 89 | 94 |

Figure 1:
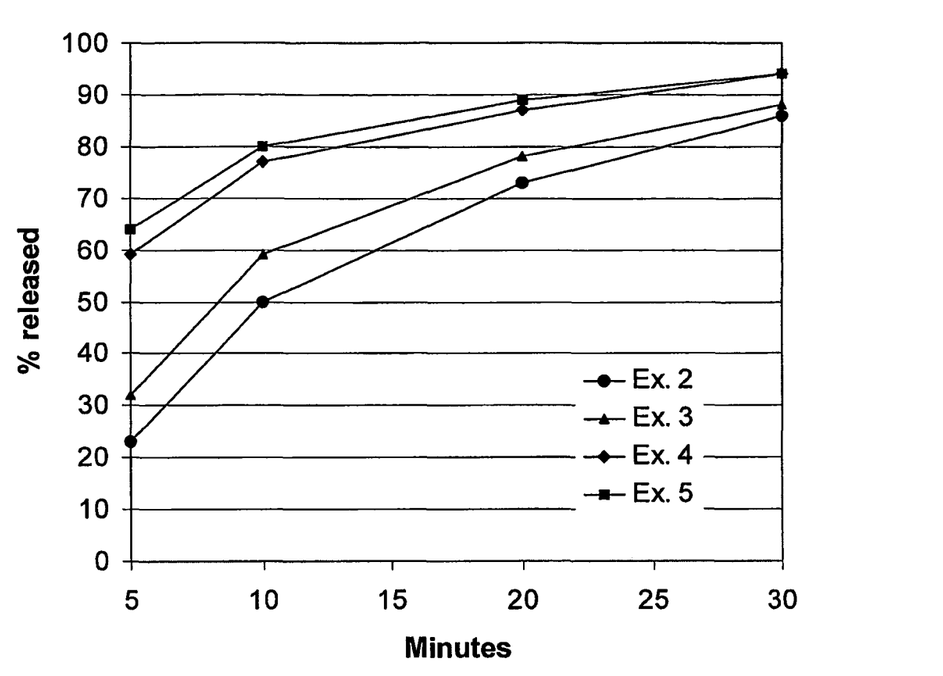
FIG. 1 illustrates release percentage as a function of time for nicotine containing chewing gums having different gum base contents.

FIG. 1 furthermore illustrates the results, and as it appears clearly from the FIGURE, a substantial increased release is unexpectedly appearing as a result of altering the percentage of elastomer- and resin compounds from 26.3% to 19.1%. In other words, a surprisingly increased release effect is obtained when lowering the content of elastomer- and resin compounds in the area of about 20 to 25% by weight of the chewing gum.

The below table 2 illustrates nicotine release of the chewing gums of examples 2-5, where the release percentages obtained by chewing gums of example 2 is given the index 100, and the release percentages obtained by chewing gums of examples 3-5 are related to example 2 and given an index based thereon.

TABLE 2

Nicotine release percentage indexed according to example 2.

| Chewing gum according to example | % in chewing gum of elastomer- and resin | Index of RELEASE at minutes | | | |
|---|---|---|---|---|---|
| | | 5 min | 10 min | 20 min | 30 min |
| Ex. 2 | 34.4 | 100 | 100 | 100 | 100 |
| Ex. 3 | 26.3 | 139 | 118 | 107 | 102 |
| Ex. 4 | 19.1 | 257 | 154 | 119 | 109 |
| Ex. 5 | 14.3 | 278 | 160 | 122 | 109 |

The perceptual release is evaluated with respect to taste of the released nicotine, and the results are presented in table 3. A scale is applied where reference is made to normal release by a conventional high gum base nicotine chewing gum of example 2.

The reference evaluation of a nicotine taste masking is referred to as A=good, B=acceptable, C=non-acceptable. The perceptual releases of nicotine at different times are mapped into the evaluation as being "good" and the examples 3-5 are evaluated relative to example 2.

TABLE 3

Sensory evaluation of the nicotine releasing chewing gums of example 2 to 5.

| Chewing gum according to example | % in chewing gum of elastomer- and resin | Evaluation of taste masking at minutes | | | |
|---|---|---|---|---|---|
| | | 5 min | 10 min | 20 min | 30 min |
| Ex. 2 | 34.4 | A | A | A | A |
| Ex. 3 | 26.3 | B | A | A | A |
| Ex. 4 | 19.1 | C | B | A | A |
| Ex. 5 | 14.3 | C | B | A | A |

It may be appreciated from table 3 that the initial increased level of released nicotine has a significant effect on the sensory evaluation.

Example 11

Evaluation of Taste Masking of Chewing Gum of Examples 6-9

The perceptual release is evaluated with respect to taste of the released nicotine, and the results are presented in table 4. A scale is applied where reference is made to normal release by a conventional high gum base nicotine chewing gum of example 2.

The reference evaluation of a nicotine taste masking is referred to as A=good, B=acceptable, C=non-acceptable. The perceptual releases of nicotine at different times are mapped into the evaluation as being "good" and the examples 7-9 are evaluated relative to example 2.

TABLE 4

Sensory evaluation of the nicotine releasing chewing gums of example 6 to 9.

| Chewing gum according to example | % in chewing gum of elastomer- and resin | Evaluation of taste masking at minutes | | | |
|---|---|---|---|---|---|
| | | 5 min | 10 min | 20 min | 30 min |
| Ex. 6 | 34.4 | A | A | A | A |
| Ex. 7 | 26.3 | A | A | A | A |
| Ex. 8 | 19.1 | B | B | A | A |
| Ex. 9 | 14.3 | B | B | A | A |

As it may be read from table 4, it has been found that a coating layer has a taste masking effect, and the effect is seen in the present examples 8 and 9 within the first five minutes of chewing.

The invention claimed is:

1. Tobacco alkaloid releasing chewing gum comprising tobacco alkaloid, gum base, and chewing gum ingredients, said gum base comprising elastomer- and resin-compounds in an amount in the range of about 2 to 26.3% by weight of said chewing gum, wherein at least 50% of the tobacco alkaloid comprised in said chewing gum prior to chewing will be released within five minutes following initiation of chewing and wherein at least 75% of the tobacco alkaloid comprised in said chewing gum prior to chewing will be released within ten minutes following initiation of chewing.

2. Tobacco alkaloid releasing chewing gum according to claim 1, wherein said chewing gum comprises tobacco alkaloid in an amount of 0.1 mg to 10 mg.

3. Tobacco alkaloid releasing chewing gum according to claim 1, wherein said chewing gum comprises tobacco alkaloid in an amount of 0.1 mg to 10 mg in the gum base of the chewing gum.

4. Tobacco alkaloid releasing chewing gum according to claim 1, wherein said tobacco alkaloid is in a form selected from tobacco alkaloid salts, tobacco alkaloid bound in a complex, or any combination thereof.

5. Tobacco alkaloid releasing chewing gum according to claim 4, wherein said complex comprises an ion exchange resin.

6. Tobacco alkaloid releasing chewing gum according to claim 5, wherein said ion exchange resin is a weakly acidic cation exchange resin.

7. Tobacco alkaloid releasing chewing gum according to claim 4, wherein said complex comprises an adsorbent.

8. Tobacco alkaloid releasing chewing gum according to claim 7, wherein said adsorbent is selected from the group consisting of finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, and any combination thereof.

9. Tobacco alkaloid releasing chewing gum according to claim 1, wherein said tobacco alkaloid is nicotine.

10. Tobacco alkaloid releasing chewing gum according to claim 9, wherein said nicotine is in a form selected from nicotine salts, nicotine free base, nicotine bound in a complex, or any combination thereof.

11. Tobacco alkaloid releasing chewing gum according to claim 10, wherein said nicotine salts are selected from the group consisting of nicotine hydrochloride, nicotine dihydrochloride, nicotine monotartrate, nicotine bitartrate, nicotine sulfate, nicotine zinc chloride, nicotine salicylate, and any combination thereof.

12. Tobacco alkaloid releasing chewing gum according to claim 1, wherein said chewing gum comprises emulsifiers in an amount in the range of 0.1% to 25% by weight of said chewing gum.

13. Tobacco alkaloid releasing chewing gum according to claim 12, wherein at least 50% of said emulsifiers are comprised in said gum base.

14. Tobacco alkaloid releasing chewing gum according to claim 12, wherein said emulsifiers are selected from the group consisting of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, and any combination thereof.

15. Tobacco alkaloid releasing chewing gum according to claim 12, wherein said emulsifiers are selected from the group consisting of cyclodextrins, polyoxyethylene (20) sorbitan monostearates, sorbitan fatty acid esters, glycerol polyethyleneglycol oxystearate, glycerol monostearate, glycerol monooleate, block copolymers of ethylene and propylene oxides, and mixtures thereof.

16. Tobacco alkaloid releasing chewing gum according to claim 1, wherein said chewing gum comprises an emulsifier having an HLB value of 7 or less.

17. Tobacco alkaloid releasing chewing gum according to claim 1, wherein said chewing gum comprises one or more emulsifiers having an HLB value of at least 7.

18. Tobacco alkaloid releasing chewing gum according to claim 1, wherein said chewing gum comprises one or more emulsifiers having an HLB value of at least 10.

19. Tobacco alkaloid releasing chewing gum according to claim 1, wherein said chewing gum comprises one or more emulsifiers of HLB value below about 7 and one or more emulsifiers of HLB value above about 7, said emulsifiers of HLB value below about 7 being applied in the gum base, and said emulsifiers of HLB value above about 7 being applied in the final chewing gum composition along with the chewing gum ingredients.

20. Tobacco alkaloid releasing chewing gum according to claim 1, wherein said resin compounds comprise natural resins in an amount in the range of 0.1 to 20% by weight of said chewing gum.

21. Tobacco alkaloid releasing chewing gum according to claim 20, wherein said natural resins comprise ester gums.

22. Tobacco alkaloid releasing chewing gum according to claim 1, wherein said resin compounds comprise natural resins in an amount in the range of 1 to 15% by weight of said chewing gum.

23. Tobacco alkaloid releasing chewing gum according to claim 1, wherein said resin compounds comprise synthetic resins in an amount in the range of 0.1 to 20% by weight of said chewing gum.

24. Tobacco alkaloid releasing chewing gum according to claim 23, wherein said synthetic resins comprise polyvinyl acetate (PVAc).

25. Tobacco alkaloid releasing chewing gum according to claim 1, wherein said resin compounds comprise synthetic resins in an amount in the range of 1 to 15% by weight of said chewing gum.

26. Tobacco alkaloid releasing chewing gum according to claim 1, wherein said resin compounds comprise terpene resins derived from alpha-pinene, beta-pinene and/or d-limonene.

27. Tobacco alkaloid releasing chewing gum according to claim 1, wherein said elastomers comprise at least 1% by weight of said chewing gum.

28. Tobacco alkaloid releasing chewing gum according to claim 1, wherein said elastomers constitute less than 20% by weight of said chewing gum.

29. Tobacco alkaloid releasing chewing gum according to claim 1, wherein said elastomers constitute an amount in the range of about 0.001 to 20% by weight of said chewing gum.

30. Tobacco alkaloid releasing chewing gum according to claim 1, wherein said elastomers are synthetic elastomers selected from the group consisting of butadiene-styrene copolymers, polyisobutadiene, isobutylene-isoprene copolymers, butyl rubber, polybutene, polybutadiene, polyisobutylene, polyvinyl acetate, polyethylene, vinyl acetate/vinyl laurate copolymer, vinyl acetate/vinyl stearate copolymer, ethylene/vinyl acetate copolymer, polyvinyl alcohol, and any mixtures thereof.

31. Tobacco alkaloid releasing chewing gum according to claim 1, wherein said elastomers are natural elastomers selected from the group consisting of natural rubber, latex, guayule, natural gums, jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang, and any combination thereof.

32. Tobacco alkaloid releasing chewing gum according to claim 1, wherein said chewing gum comprises pH controlling components.

33. Tobacco alkaloid releasing chewing gum according to claim 32, wherein said pH controlling components are selected from the group consisting of sodium carbonate, sodium hydrogen carbonate, potassium carbonate, potassium hydrogen carbonate, dipotassium phosphate, potassium citrate, and any combination thereof.

34. Tobacco alkaloid releasing chewing gum according to claim 32, wherein said pH controlling components comprise an amount in the range of 0.1% to 5% by weight of said chewing gum.

35. Tobacco alkaloid releasing chewing gum according to claim 32, wherein said pH controlling components provide a pH value in the range of 7.4 to 10 in the buccal cavity of a user of said chewing gum.

36. Tobacco alkaloid releasing chewing gum according to claim 1, wherein said chewing gum comprises a coating.

37. Tobacco alkaloid releasing chewing gum according to claim 36, wherein said coating is a hard coating.

38. Tobacco alkaloid releasing chewing gum according to claim 36, wherein said coating is a soft coating or a film coating.

39. Tobacco alkaloid releasing chewing gum according to claim 36, wherein said coating comprises a further amount of tobacco alkaloid.

40. Tobacco alkaloid releasing chewing gum according to claim 36, wherein said coating has a weight above 20 mg.

41. Tobacco alkaloid releasing chewing gum according to claim 36, wherein said coating makes up more than 2% by weight of the chewing gum.

42. Tobacco alkaloid releasing chewing gum according to claim 1, wherein said chewing gum comprises a coating comprising a portion of at least 100 milligrams and wherein said portion comprises high-intensity sweetener.

43. Tobacco alkaloid releasing chewing gum according to claim 42, wherein said coating comprises a portion of at least 100 milligrams and wherein said portion comprises bulk sweetener.

44. Tobacco alkaloid releasing chewing gum according to claim 42, wherein said coating comprises a portion of at least 100 milligrams and wherein said portion comprises flavor.

45. Tobacco alkaloid releasing chewing gum according to claim 1, wherein said chewing gum comprises sweeteners.

46. Tobacco alkaloid releasing chewing gum according to claim 45, wherein said sweeteners comprise bulk sweeteners, sugar sweeteners, sugar substitute sweeteners, artificial sweeteners, high-intensity sweeteners, or any combination thereof.

47. Tobacco alkaloid releasing chewing gum according to claim 1, wherein said chewing gum comprises one or more flavoring agents.

48. Tobacco alkaloid releasing chewing gum according to claim 47, wherein said flavoring agents comprise natural and synthetic flavorings.

49. Tobacco alkaloid releasing chewing gum according to claim 47, wherein said flavoring agents comprise essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, eucalyptus, mint, or any combination thereof.

50. Tobacco alkaloid releasing chewing gum according to claim 1, wherein said chewing gum comprises filler.

51. Tobacco alkaloid releasing chewing gum according to claim 50, wherein said filler is comprised within said gum base.

52. Tobacco alkaloid releasing chewing gum according to claim 50, wherein said filler is incorporated in said chewing gum along with said chewing gum ingredients.

53. Tobacco alkaloid releasing chewing gum according to claim 1, wherein said chewing gum has a weight in the range of 0.1 to 10 grams.

54. Tobacco alkaloid releasing chewing gum according to claim 1, wherein said chewing gum is multimodular.

55. Tobacco alkaloid releasing chewing gum according to claim 1, wherein said chewing gum comprises a tobacco alkaloid releasing module, which is a substantially gum base free module.

56. Tobacco alkaloid releasing chewing gum according to claim 1, wherein said chewing gum is a chewing gum tablet.

57. Tobacco alkaloid releasing chewing gum according to claim 1, wherein said chewing gum comprises further active ingredients.

58. Tobacco alkaloid releasing chewing gum according to claim 57, wherein an amount of said further active ingredients is within the range of about 0.01 mg to 1000 mg.

59. Tobacco alkaloid releasing chewing gum according to claim 57, wherein said further active ingredients are selected from the group consisting of dental agents and agents for treating pain, headache, or weight-gain.

60. Tobacco alkaloid releasing chewing gum according to claim 57, wherein said further active ingredients are selected from the group consisting of cetirizine, loratadine, phenyleferin, paracetamol, ibuprofen, calciumcarbonat, vitamin D3, sumatriptan, ketoprofen, naproxen, morphine, cimetidine, famotidine, ranitidine, chlorpheneramine, dextrometorphane, metformine, and any combination thereof.

61. Tobacco alkaloid releasing chewing gum according to claim 1, wherein said chewing gum is prepared by compression of said chewing gum.

62. Tobacco alkaloid releasing chewing gum according to claim 1, wherein at least 85% of the tobacco alkaloid comprised in said chewing gum prior to chewing will be released within twenty minutes following initiation of chewing.

63. Tobacco alkaloid releasing chewing gum according to claim 62, wherein at least 90% of the tobacco alkaloid comprised in said chewing gum prior to chewing will be released within thirty minutes following initiation of chewing.

64. Tobacco alkaloid releasing chewing gum according to claim 1, wherein said tobacco alkaloid is comprised in tobacco powder.

* * * * *